US008962339B2

(12) United States Patent
Peng et al.

(10) Patent No.: US 8,962,339 B2
(45) Date of Patent: Feb. 24, 2015

(54) FLUORESCENT PROBE COMPOUNDS, PREPARATION METHOD AND APPLICATION THEREOF

(75) Inventors: Xiaojun Peng, Dalian (CN); Jiangli Fan, Dalian (CN); Honglin Li, Dalian (CN); Jingyun Wang, Dalian (CN); Shiguo Sun, Dalian (CN)

(73) Assignees: Dalian University of Technology, Dalian, Liaoning (CN); Dalian Chromas Bioscience Co., Ltd., Dalian, Liaoning (CN)

(*) Notice: Subject to any disclaimer, the term of this patent is extended or adjusted under 35 U.S.C. 154(b) by 374 days.

(21) Appl. No.: 13/521,047

(22) PCT Filed: Dec. 6, 2010

(86) PCT No.: PCT/CN2010/001972
§ 371 (c)(1),
(2), (4) Date: Jul. 7, 2012

(87) PCT Pub. No.: WO2011/085533
PCT Pub. Date: Jul. 21, 2011

(65) Prior Publication Data
US 2012/0288947 A1   Nov. 15, 2012

(30) Foreign Application Priority Data
Jan. 15, 2010   (CN) .......................... 2010 1 0010135

(51) Int. Cl.
*G01N 21/76*   (2006.01)
*C07D 491/107*   (2006.01)
(Continued)

(52) U.S. Cl.
CPC ............... *C07F 9/6561* (2013.01); *C09K 11/06* (2013.01); *G01N 21/643* (2013.01); *G01N 21/75* (2013.01);
(Continued)

(58) Field of Classification Search
CPC ..... G01N 31/22; G01N 33/84; A61K 31/295; A61K 31/7016; A61K 33/26; C07D 487/10; C07D 491/10; C07D 495/10; C07D 209/34; C07D 335/06
USPC ............................................ 436/84; 548/410
See application file for complete search history.

(56) References Cited

FOREIGN PATENT DOCUMENTS

CN   101270121 A   9/2008
CN   101735277 A   6/2010

OTHER PUBLICATIONS

A highly sensitive and selective off-on chemosensor for the visual detection of Pd2+ in aqueous media Yanmei Zhou, Juli Zhang, Hua Zhou,Qingyou Zhang, Tongsen Ma, Jingyang Niu Sensors and Actuators B 171-172 (2012) 508-514.*
A palladium(II) complex of a new iminophosphine ligand derived from diethylenetriamine and 2-(diphenylphosphine)benzaldehyde Scott E. Watkins, Donald C. Craig, Stephen B. Colbran Inorganica Chimica Acta 307 (2000) 134-138.*
(Continued)

*Primary Examiner* — Krishnan S Menon
*Assistant Examiner* — Dwan A Gerido
(74) *Attorney, Agent, or Firm* — Novick, Kim & Lee, PLLC; Allen Xue

(57) ABSTRACT

The present invention discloses a fluorescent probe compound which solved the problem of fluorescence quenching by $Pd^{2+}$, and its preparation method and use as well. Excitation and emission wavelengths of the probe compound are in visible light region. The probe compound is highly sensitive and displays good selectivity for $Pd^{2+}$ in near-neutral pH range. In detection of $Pd^{2+}$ in 0-10 ppb level, fluorescence is evidently enhanced, and $Pd^{2+}$ in the level as low as 5 nM can be detected. Fluorescence intensity is well linearly correlated to $Pd^{2+}$ concentration. The probe compound can be used for detection of contaminating palladium and residual palladium in drug, soil, water sample and reactor.

8 Claims, 8 Drawing Sheets

(51) Int. Cl.
*C07F 9/6561* (2006.01)
*C09K 11/06* (2006.01)
*G01N 21/64* (2006.01)
*G01N 21/75* (2006.01)
*G01N 21/77* (2006.01)

(52) U.S. Cl.
CPC . *C09K 2211/1007* (2013.01); *C09K 2211/1029* (2013.01); *C09K 2211/1088* (2013.01); *G01N 2021/6439* (2013.01); *G01N 2021/7786* (2013.01)
USPC .......................................... 436/84; 548/410

(56) References Cited

OTHER PUBLICATIONS

Huo, Fang-Jun, et al., "A rhodamine-based dual chemosensor for the visual detection of copper and the ratiometric fluorescent detection of vanadium", Dyes and Pigments, Dec. 24, 2009, pp. 50-55, vol. 86, No. 1, Elsevier, Amsterdam.

Zheng, Al Fang, et al., "A novel fluorescent distinguished probe for Cr(VI) in acqueous solution", Spectrochimica Acta, Part A: Molecular and Biomolecular Spectroscopy, 2009, pp. 265-270, vol. 74, No. 1, Elsevier, Amsterdam.

\* cited by examiner

1=probe, 2=PdCl$_2$, 3=Pd(OAc)$_2$, 4=Pd(NH$_3$)$_4$Cl$_2$,
5=Pd(COD)Cl$_2$, 6=Pd(PPh$_3$)$_2$Cl$_2$, 7=Pd(PPh$_3$)$_4$ Detection of $Pd^{2+}$ in drug Detection of $Pd^{2+}$ in soil Detection of $Pd^{2+}$ in water samples (tap water, pool water and sea water)

Detection of residual palladium in reactor

1=probe, 2= PdCl₂, 3=Pd(OAc)₂

FLUORESCENT PROBE COMPOUNDS, PREPARATION METHOD AND APPLICATION THEREOF

TECHNICAL FIELD

The present invention relates to a fluorescence probe compound for palladium ion detection in fine chemical field as well as its preparation method and use.

BACKGROUND ART

Palladium is widely used in various materials such as dental crowns, catalysts, fuel cells and jewelry. The application of palladium as an automobile catalytic converter has evidently controlled the pollution of vehicle exhaust, but at the same time, a significant quantity of palladium deposited in the roadside soil (<0.3 ppm) and plants. Rain may wash them into river, lake and sea which would lead to the pollution of water system. Additionally, palladium is commonly employed as an efficient catalyst for the synthesis of complex molecules, therefore it plays a very important role in pharmaceutical industry. Despite the wide application in catalytic reaction, a high level of residual palladium is often found in the resultant product (typically 300 to 2000 ppm) and in the reactor, which thus may be a health hazard. For example, palladium content in drugs is limited to 5 to 10 ppm. Therefore, a convenient, fast, highly sensitive and selective detection method for palladium is urgently needed.

Traditional detection methods for palladium, such as atomic absorption spectrometry, plasma emission spectrometry, solid phase microextraction-high performance liquid chromatography and x-ray fluorescence, usually suffer from high cost due to complicated pretreatment process for the sample and operation by highly trained individuals that limited their application. Fluorescence probe has attracted much attention due to high sensitivity, good selectivity, fast response and capability for the visual detection. As an open-shell transition-metal ion, $Pd^{2+}$ displays an evident fluorescence quenching. Hence most of probes for $Pd^{2+}$ detection are designed by colorimetric and fluorescence-quenched methods. There are only three fluorescence-enhanced $Pd^{2+}$ probes reported. Generally, compared with the detection for quenched fluorescence, the detection for increased fluorescence is more reliable, lower in detection limit and better in properties. So how to avoid fluorescence-quenching of $Pd^{2+}$ is crucial to $Pd^{2+}$ probe. Here we synthesized a rhodamine-based fluorescence-enhanced probe based on triphenylphosphine ligand coordinating $Pd^{2+}$ for the first time, which can provide us both fluorometric and colorimetric methods for visual detection of $Pd^{2+}$.

There have been three examples of fluorescence-enhanced probes specific for $Pd^{2+}$ were reported: the first one is designed based on thioether-maleonitrile ligand as receptor; the second one is designed based on Tsuji-Trost allylic oxidation insertion reaction; the third one is the rhodamine probe designed by our research team based on allyl group coordinating $Pd^{2+}$. They all display their own disadvantages: the first thioether-maleonitrile fluorescence probe displays a fluorescence spectrum change after coordination with $Pd^{2+}$, but excitation wavelength thereof is not in visual light area and can not be used for $Pd^0$ detection as well (Thomas Schwarze, Holger Muller, Carsten Dosche, Tillmann Klamroth, Wulfhard Mickler, Alexandra Kelling, Hans-Gerd Lohmannsroben, Peter Saalfrank and Hans-Jurgen Holdt, Angew. Chem. Int. Ed., 2007, 46, 1671-1674); the second allylic oxidation insertion reaction-based fluorescence probe can not avoid the interference from $Pt^{2+}$ (Fengling Song, Amanda L. Garner and Kazunori Koide, J. Am. Chem. Soc., 2007, 129(41), 12354-12355); although the third allyl coordinating $Pd^{2+}$-based probe has solved the problems of the above-mentioned two probes, it still displays a disadvantage of a long balance time (Honglin Li, Jiangli Fan, Jianjun Du, Kexin Guo, Shiguo Sun, Xiaojian Liu and Xiaojun Peng, Chem. Commun., 2010, DOI: 10. 1039/b916915f).

SUMMARY OF THE INVENTION

Therefore, it is still in great demand of a novel probe compound for palladium ion detection to avoid disadvantages mentioned above currently.

In this invention, a novel rhodamine-based fluorescence-enhanced probe for the detection of $Pd^{2+}$ and $Pd^0$ in a low level was designed and synthesized to improve the disadvantages of the reported colorimetric and fluorescence-quenched methods.

The applicant of the present invention found that, the coordination of palladium ion can promote the opening of spiro-ring of the rhodamine-based probe synthesized in the present invention, which evidently enhanced UV absorption and fluorescence emission and the recognition process could finish within 20 s. Therefore, the rhodamine-based probe of the present invention can be used for selective detection of $Pd^{2+}$/$Pd^0$ in ppb level with an enhanced fluorescence signal thus to conquer the disadvantages in normal methods.

In the present invention, the rhodamine-based fluorescence probe was used, the coordination of palladium ion induced the 'ring-open' reaction of the probe and an evident color change (from colorless to purple) and enhanced fluorescence signal was found which could be seen by naked eyes.

For the rhodamine-based probe designed on the basis of 'coordination to ring-open' mechanism, the 'ring-open' reaction can be induced to take place after detecting palladium ion, which results in an evident enhancement in fluorescence and UV absorption. The recognition reaction is very mild and can complete fastly at room temperature with specific selectivity. Moreover, the probe exhibits good sensitivity, displays an evident fluorescence enhancement even when palladium ion is in ppb level, and shows a good linear relation between the fluorescence enhancement and the concentration of palladium ion. Applications for detecting residual palladium ion in drug, water sample, soil and reactor can be performed using the probe.

The rhodamine-based fluorescence probe compound for $Pd^{2+}$ detection described in this invention includes the following general formula I.

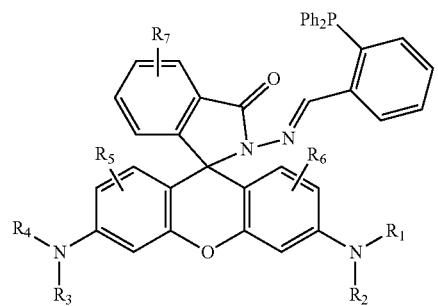

wherein, $R_1$, $R_2$, $R_3$ and $R_4$ are each independently selected from the group consisting of H, $C_{1-6}$ alkyl, $C_{1-6}$ alkyl substituted phenyl, $C_{1-6}$ alkyl substituted naphthyl, halogen, $OR_8$, $N(R_8)_2$, CN, $(CH_2CH_2O)_nH$, $(CH_2)_m COOM$ and $(CH_2)_m SO_3M$;

$R_5$, $R_6$ and $R_7$ are each independently selected from the group consisting of H, $C_{1-6}$ alkyl, $C_{1-6}$ alkyl substituted phenyl, $C_{1-6}$ alkyl substituted naphthyl, halogen, hydroxyl, mercapto group, cyano group, nitro group, heterocyclic group, halogenated alkyl, alkyl amino group, acylamino group, $OR_8$, $N(R_8)_2$, $(CH_2CH_2O)_nH$, $(CH_2)_m COOM$ and $(CH_2)_m SO_3M$;

$R_8$ is selected from the group consisting of H, $C_{1-6}$ alkyl, $C_{1-6}$ alkyl substituted phenyl, $C_{1-6}$ alkyl substituted naphthyl, halogen, CN, $(CH_2CH_2O)_nH$, $(CH_2)_mCOOM$ and $(CH_2)_mSO_3M$;

n and m are integer from 0 to 6;

M is selected from the group consisting of H, K, Na, Li, $NH_4$, $NH_3R_9$, $NH_2(R_9)_2$, $NH(R_9)_3$ and $N(R_9)_4$;

and $R_9$ is selected from the group consisting of H, $C_{1-6}$ alkyl and $CH_2CH_2OH$.

In addition, the present invention further provided a method for synthesizing the above-mentioned compound of Formula I, which includes the following steps:

(1) synthesis of intermediate II by reacting rhodamine fluorescence dye of formula I' with lactone-ring and hydrazine hydrate II: the rhodamine fluorescence dye of formula I' is added into an alcohol solvent and stirred at room temperature so that the rhodamine fluorescence dye is evenly dispersed in the alcohol solvent; hydrazine hydrate in an excessive amount stoichiometrically is added dropwise; after finishing the addition of hydrazine hydrate, the mixture is heated to reflux the solvent and reacted until the reaction solution becomes clear; after the solution is cooled down to room temperature, the solvent is removed by evaporation; acid is added to adjust pH to 2 to 5 and then base solution is added under stirring to adjust pH to 9 to 10 to obtain precipitation; the obtained precipitation is filtered and washed, dried under vacuum and purified by recrystallization.

The preferable rhodamine dye with lactone-ring is but not limited to rhodamine B, rhodamine 110, rhodamine 6G, rhodamine 3GB, rhodamine 3GO, rhodamine 123 and so on.

The preferable hydrazine hydrate is 50% or 85% aqueous solution which is commercial available.

The preferable alcohol solvent is but not limited to methanol, ethanol, propanol, and isopropanol. The advantage of these alcohols is low boiling point along with low reflux temperature which is convenient for reflux reaction and solvent removal by evaporation after reaction.

The rhodamine dye is usually a solid at room temperature. In order to achieve good reaction effect with hydrazine hydrate, after the rhodamine dye is added into the alcohol solvent, stirring is necessary and strong stirring is preferred to evenly disperse the rhodamine dye in the alcohol solvent, and it is preferred that the rhodamine dye is dissolved completely in the alcohol solvent.

After the rhodamine dye is dispersed or dissolved in the alcohol solvent, hydrazine hydrate in a state of aqueous solution was added dropwise. An excessive amount of hydrazine hydrate relative to that of the rhodamine dye is preferred for good performance of the reaction.

After finishing the addition of hydrazine hydrate, the mixture is heated to reflux the solvent and reacted until the reaction solution becomes nearly clear. The preferred reflux time is 1 to 3 h. Then the solution is cooled down to room temperature and the solvent is removed by evaporation. After that, acid (hydrochloric acid is preferred) is added to adjust pH to 2 to 5 and then base solution (aqueous base solution is preferred, and NaOH aqueous solution is more preferred) is added under stirring to adjust pH to 9 to 10 to obtain precipitation. The obtained precipitation is filtered and preferably washed 3 times with deionized water, dried under vacuum and preferably recrystallized with ethanol. The product is characterized through NMR and TOF MS. $^1H$ NMR ($CDCl_3$) δ (ppm): 5.73 (s, 2H, $NH_2$) (the shift of H at other position is different according to different rhodamine dye.)

(2) synthesis of product of formula I by reacting the intermediate II obtained in (1) and 2-diphenylphosphinobenzaldehyde: the intermediate II is added into reactor, and then ethanol solvent and a stoichiometric amount of 2-diphenylphosphinobenzaldehyde are added; the mixture is stirred under reflux and reacted for 5 to 10 h; the solvent is removed by evaporation, and purification is carried out through column chromatography to obtain the compound of formula I.

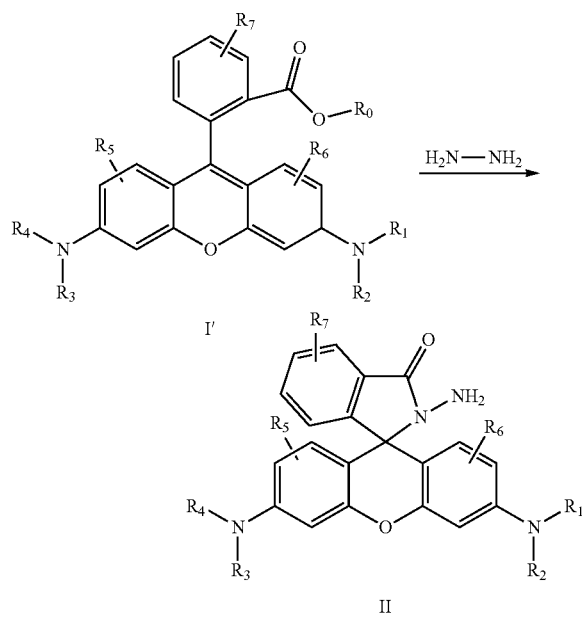

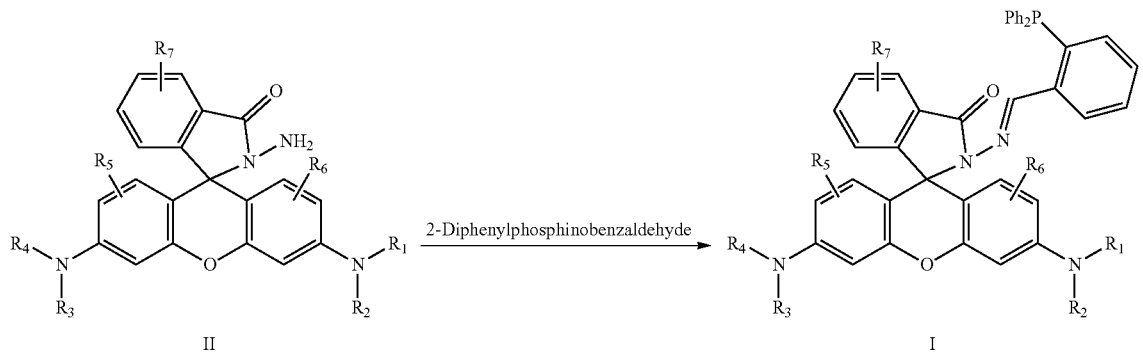

The preferred solvent in this step is ethanol which is convenient for reflux, reaction and solvent removal after reaction.

Commercial available 2-diphenylphosphinobenzaldehyde is preferred. An addition amount equivalent to that of the intermediate II is preferred which is convenient for the purification after reaction.

The reaction is preferred to be carried out under inert gas circumstance which would give a higher yield.

The reaction time is preferred 5 to 10 h, and 10 h is more referable.

The solvent is removed by evaporation after the reaction is completed. The product is purified through column chromatography preferably using CH2Cl2/EtOAc as eluting solution. The product is characterized by NMR and TOF MS. 9.17 (d, 1H, J=6.4 Hz, NNCH), 8.11 (s, 1H, $C_6H_4$), 7.99 (d, 1H, $C_6H_4$), 7.39 (s, 2H, $C_6H_4$), 7.25 (d, 3H, J=7.2 Hz, $C_6H_4$), 7.19 (d, 4H, J=7.6 Hz, $C_6H_4$), 7.10 (t, 1H, J=7.2 Hz, $C_6H_4$), 7.01 (t, 5H, J=6.4 Hz, $C_6H_4$), 6.79 (s, 1H, $C_6H_4$) (the shift of H at other position is different according to different rhodamine dye.)

$R_0$ is different according to different rhodamine dye and is generally selected from H or alkyl chain with different length; $R_1$, $R_2$, $R_3$, $R_4$, $R_5$, $R_6$, $R_7$, $R_8$, m, n, M and $R_9$ are defined as those in the compound of formula I.

The obtained fluorescence dye can be separated and purified to achieve needed purity through the common methods in this field.

All the raw materials used in the present invention are commercial available or can be easily prepared from the known raw materials through known methods in this field.

It should be known that, some of the substituents in the ring in this invention could be introduced by standard aromatic ring substitution reaction or be produced by normal functional group modification, before or after the steps mentioned above, and all of these should be included in the present invention. The reaction and the modification include, for example, introduction of substituent by aromatic ring substitution reaction, reduction of substituent, alkylation of substituent and oxidation of substituent. The reagent and reaction condition used in the process are known in this field. The aromatic ring substitution reaction, for example, includes the introduction of nitro group by concentrated nitric acid, the introduction of acyl group by acyl halide and Lewis acid (e.g. $AlCl_3$) under Friedel Crafts condition, the introduction of alkyl group by alkyl halide and Lewis acid (e.g. $AlCl_3$) under Friedel Crafts condition, and the introduction of halogen group. The modification, for example, includes reduction of nitro group to amino group by catalytic hydrogenation with nickel catalyst or heat-treatment with iron in the presence of HCl, and oxidation of alkylthio group to alkylsulfinyl group or alkyl sulfonyl group.

The terms used in the present invention have the following definitions, unless otherwise stated.

The term "alkyl" used herein includes straight and branched alkyl groups. In reference to a single alkyl such as "propyl", it specifically means a straight alkyl group, while in reference to a single branched alkyl such as "isopropyl", it specifically means a branched alkyl group. For example, "$C_{1-6}$ alkyl" includes $C_{1-4}$ alkyl, $C_{1-3}$ alkyl, methyl, ethyl, n-propyl, isopropyl and tert-butyl. The similar rule is also applicable for other groups used in the present specification.

The term "halogen" used herein includes fluorine, chlorine, bromine and iodine.

In addition, the present invention also provides a detection method of $Pd^{2+}$ using the compound of formula I: the probe compound is dissolved in DMSO to prepare a 10 mM stock solution and an appropriate amount of the stock solution is added to Pd-containing ethanol solution to make the final concentration of the probe compound as 10 μM, and then fluorescence intensity is measured.

The effects of the present invention are those: the probe compound in this invention is pH-insensitive and has high sensitivity, good selectivity and fast response, and can be used for analysis of palladium-containing drug, soil and water sample, and can also be utilized for visual detection of residual palladium in reaction as well. According to the description above and the common knowledge known by the one skilled in the art, it can be known that the rhodamine-based fluorescence probe compound has advantages described below.

(1) The fluorescence probe compound in this invention has excitation and emission spectra in visible region, high fluorescence quantum yield, low sensitivity to polarity of solvent, and good chemical/photostability.

(2) The fluorescence probe compound in this invention is designed based on ring-opening mechanism induced by $Pd^{2+}$ coordination which displays large fluorescence enhancement of about 400 folds. The fluorescence probe compound shows specific selectivity to $Pd^{2+}$ and is insensitive to pH. In the pH range of 5.2 to 10.5, pH change nearly does not affect the fluorescence detection of $Pd^{2+}$.

(3) The fluorescence probe compound in this invention displays high sensitivity that fluorescence intensity is well linearly correlated to $Pd^{2+}$ concentration even in ppb level and 5 nM $Pd^{2+}$ can be detected.

(4) Fast response. Recognition of the probe compound in this invention for $Pd^{2+}$ is so fast that it can be completed within 20 s, which is the fastest responsive $Pd^{2+}$ probe reported in references.

(5) The probe compound in this invention provides us both fluorometric and colorimetric methods, which demonstrates potential applications in the detection of contaminating $Pd^{2+}$ and residual $Pd^{2+}$ of drug, water sample, soil and reactor.

MODE FOR CARRYING OUT THE INVENTION

Figure 1:
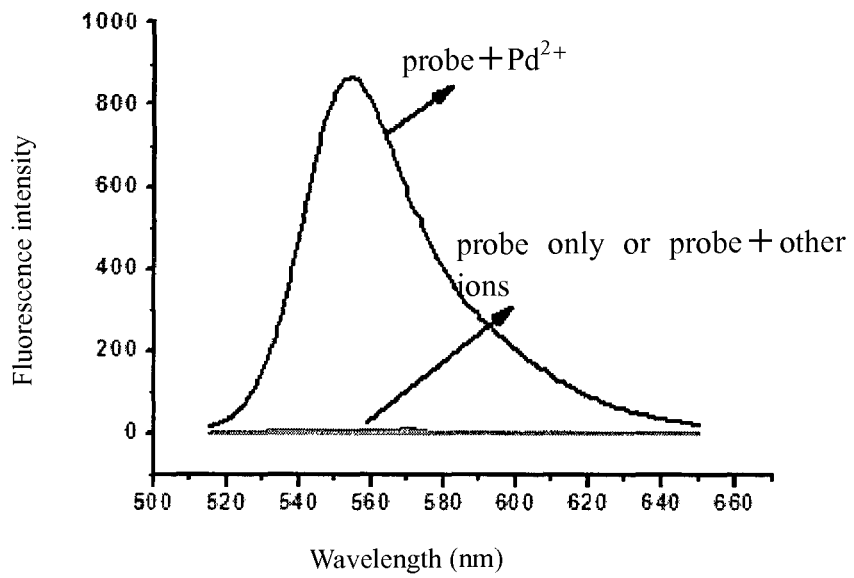
FIG. 1 is fluorescence emission spectrum of fluorescence probe compound RPd1 in Example 1 coordinating $Pd^{2+}$ over other common metal ions. Concentrations of RPd1 and the metal ions are 10 μM, respectively. X-axis is wavelength (nm) and Y-axis is fluorescence intensity. The instrument is fluorospectrophotometer, model: LS 55.

The fluorescence probe compound in this invention shows the potential application for $Pd^{2+}$ detection in drug, soil and water sample, and for visual detection of residual palladium in reactor. Details will be described briefly below.

Pd-Containing Drug Sample Analysis:

A commercial available paracetamol tablet was dissolved in ethanol with stirring overnight to prepare a 10 mg/ml drug sample. After insoluble ingredients were filtered, the obtained solution was spiked with different amount of palladium ion (0-10 ppm, calculated based on the weight of paracetamol). Then RPd1 (10 μM) was added, followed by the measurement of fluorescence signal.

Pd-Containing Soil Sample Analysis:

Soil was heated in an oven then it was suspended in ethanol with stirring overnight to prepare a 10 mg/ml soil sample. After insoluble ingredients were filtered, the obtained solution was spiked with different amount of palladium ion (0-10 ppm, calculated based on the weight of soil). Then RPd1 (10 μM) was added, followed by the measurement of fluorescence signal.

Pd-Containing Water Sample Analysis:

In water samples (tap water, pool water and sea water), the same amount of ethanol was added. After insoluble ingredients were filtered, the obtained solutions were spiked with different amount of palladium ion (0-1 ppm, calculated based on the weight of water). Then RPd1 (10 μM) was added, followed by the measurement of fluorescence signal.

Visual Detection of Residual Palladium in Reactor:

$K_2CO_3$ (10 mg) and THF (10 ml) were added into three reactors. $PdCl_2$ and $Pd(AcO)_2$ (10 mg in both cases) were then added into two of the three reactors, respectively. The mixtures were stirred at room temperature for 1 h and then removed from the reactor. The reactors were brushed with detergent solution, and then washed with water and acetone for three times, respectively. RPd1 ethanol solution (10 μM) was added into these reactors and stirred followed by the measurement of fluorescence.

EXAMPLE 1

The Synthesis of Fluorescence Probe Compound RPd1

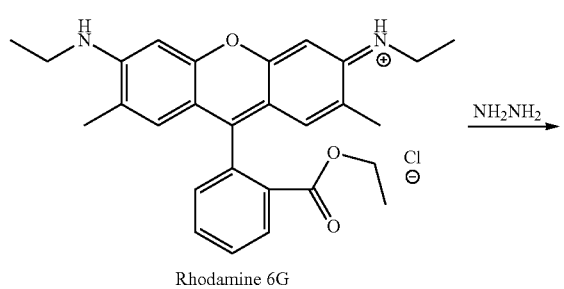

Rhodamine 6G

-continued

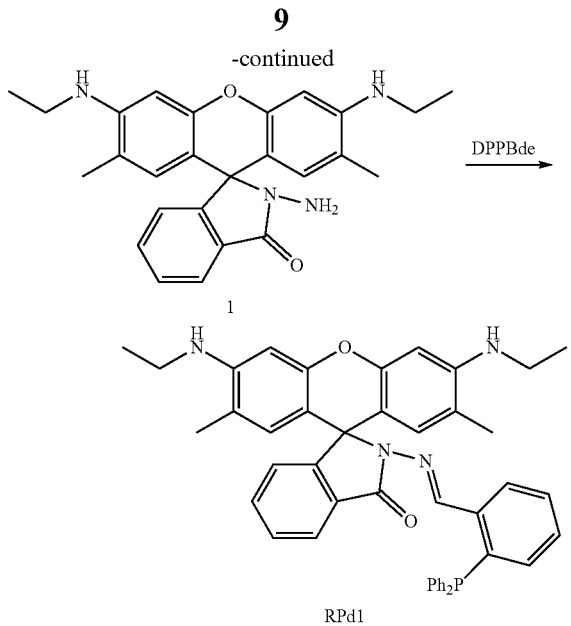

RPd1

(1) The Synthesis of Intermediate 1:

Rhodamine 6G (1.2 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.64 g intermediate 1, yield 60.0%. $^1$H NMR (400 MHz $CDCl_3$) δ (ppm): 1.21 (t, 6H), 1.87 (s, 6H), 3.14 (t, 4H), 4.23 (s, 2H), 5.01 (s, 1H), 6.10 (s, 2H), 6.27 (s, 2H), 6.95 (d, J=8 Hz, 1H), 7.47 (d, J=8 Hz, 1H), 7.48 (d, J=8 Hz, 1H), 7.85 (t, 1H); $^{13}$C NMR (400 MHz, $CDCl_3$), δ: 12.7, 19.8, 44.5, 66.04, 98.09, 103.78, 108.17, 123.98, 124.07, 126.58, 128.62, 134.97, 149.21, 152.64, 152.87, 165.87; TOF MS (ES): m/z Calcd for $C_{26}H_{28}N_4O_2^+$: 428.2212. Found: 428.2234.

(2) The Synthesis of Fluorescence Probe Compound RPd1:

The intermediate 1 (0.22 g, 0.5 mmol) and 2-diphenylphosphinobenzaldehyde (DPPBde, 0.15 g, 0.5 mmol) were added into a 100 ml single-necked flask, and then 50 ml ethanol was added. The mixture was refluxed under stirring for 10 h in nitrogen environment, and then the solvent was removed under reduced pressure. The product was purified through column chromatography with $CH_2Cl_2$/EtOAc (v/v, 5/1) as elution solution to produce 0.27 g light pink solid RPd1, yield 77.9%. $^1$H NMR (400 MHz, $CDCl_3$), δ (ppm): 9.17 (d, 1H, J=6.4 Hz, NNCH), 8.11 (s, 1H, $C_6H_4$), 7.99 (d, 1H, $C_6H_4$), 7.39 (s, 2H, $C_6H_4$), 7.25 (d, 3H, J=7.2 Hz, $C_6H_4$), 7.19 (d, 4H, J=7.6 Hz, $C_6H_4$), 7.10 (t, 1H, J=7.2 Hz $C_6H_4$), 7.01 (t, 5H, J=6.4 Hz, $C_6H_4$), 6.79 (s, 1H, $C_6H_4$), 6.37 (s, 2H, Xanthene-H), 6.30 (s, 2H, Xanthene-H), 3.15 (q, 4H, J=6.8 Hz, $CH_2$), 2.05 (s, 6H, $CH_3$), 1.26 (t, 6H, J=6.4 Hz, $CH_3$); $^{13}$C NMR (100 MHz, $CDCl_3$), $δ_C$ (ppm): 165.70, 153.20, 151.16, 147.46, 144.66, 139.91, 137.40, 135.31, 133.75, 129.64, 129.08, 128.30, 127.78, 126.41, 125.15, 123.59, 118.06, 105.87, 97.38, 65.75, 60.50, 38.44, 32.32, 29.81, 26.52, 23.56, 21.16, 16.81, 14.90, 14.32. TOF MS (ES): m/z Calcd for $C_{45}H_{42}N_4O_2P^+$: 701.3045. Found: 701.3033.

EXAMPLE 2

Selectivity Test of Fluorescence Probe Compound RPd1 to $Pd^{2+}$

The synthesized compound RPd1 was adopted to test the selectivity to $Pd^{2+}$. RPd1 (10 μM) was added into ethanol solution containing the same amount of metal ion, and then the fluorescence spectrum was tested with excitation wavelength of 505 nm and emission wavelength of 552 nm, the result is shown in FIG. 1. From FIG. 1, it can be seen that, RPd1 exhibits good selectivity to $Pd^{2+}$ and large fluorescence and UV absorption enhancement is induced by $Pd^{2+}$ without the interference from $Na^+$, $K^+$, $Ca^{2+}$, $Mg^{2+}$, $Cu^{2+}$ and so on. X-axis is wavelength (nm) and Y-axis is fluorescence intensity. The instrument is fluorospectrophotometer, model: LS 55.

EXAMPLE 3

Figure 2:
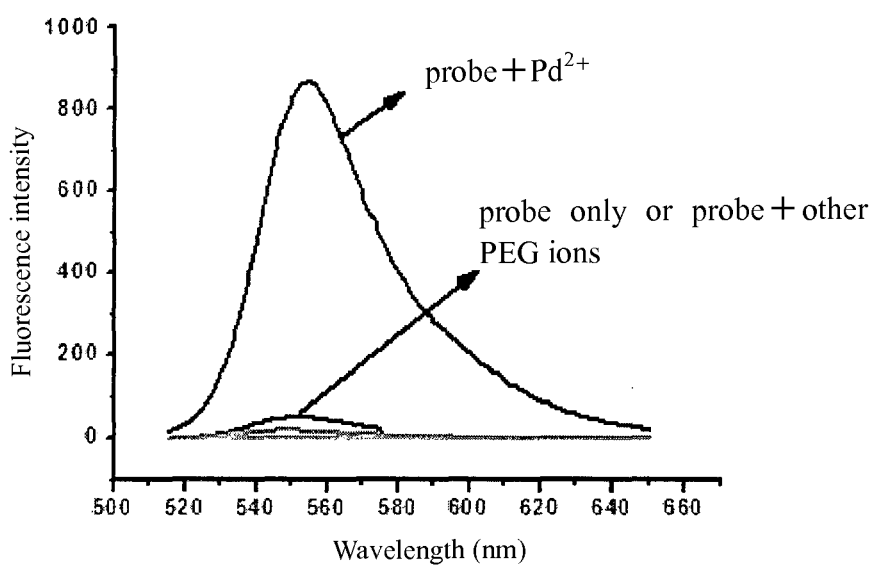
FIG. 2 is fluorescence emission spectrum of RPd1 coordinating $Pd^{2+}$ over other platinum group element (PGE) ions. Concentrations of RPd1 and the platinum group metal ions are 10 μM, respectively. X-axis is wavelength (nm) and Y-axis is fluorescence intensity. The instrument is fluorospectrophotometer, model: LS 55.

Selectivity Test of Fluorescence Probe Compound RPd1 to Common Platinum Group Metal Ion The synthesized compound RPd1 was adopted to test the selectivity to $Pd^{2+}$. RPd1 (10 μM) was added into ethanol solution containing the same amount of common platinum group element (PGE) ion, and then the fluorescence spectrum was tested with excitation wavelength of 505 nm and emission wavelength of 552 nm, the result is shown in FIG. 2. From FIG. 2, it can be seen that, RPd1 exhibits good selectivity to $Pd^{2+}$ and large fluorescence and UV absorption enhancement is induced by $Pd^{2+}$ without the interference from $Pt^{2+}$, $Rh^{3+}$, $Ru^{3+}$. X-axis is wavelength (nm) and Y-axis is fluorescence intensity. The instrument is fluorospectrophotometer, model: LS 55.

EXAMPLE 4

Figure 3:
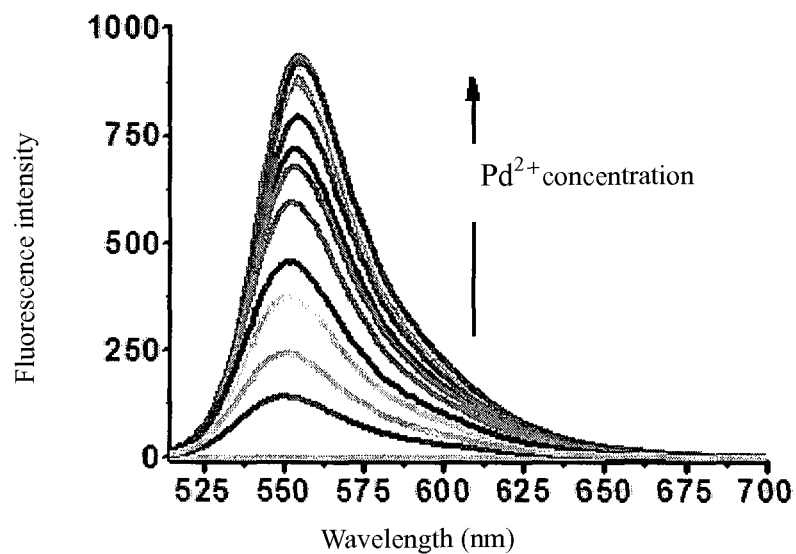
FIG. 3 is fluorescence emission spectrum of RPd1 versus $Pd^{2+}$ concentration. X-axis is wavelength (nm) and Y-axis is fluorescence intensity. Concentration of RPd1 is 10 μM, and concentrations of $Pd^{2+}$ are 0, 1, 2, 3, 4, 5, 6, 7, 8, 9, 10, 11, 13, 15 and 20 μM, respectively. The instrument is fluorospectrophotometer, model: LS 55.

The Fluorescence Emission Spectra Change of RPd1 Versus Different Concentration of $Pd^{2+}$ FIG. 3 displays the fluorescence emission spectra change of RPd1 versus different concentration of $Pd^{2+}$. X-axis is wavelength (nm) and Y-axis is fluorescence intensity. The concentration of RPd1 is 10 μM, and the concentrations of $Pd^{2-}$ are 0, 1, 2, 3, 4, 5, 6, 7, 8, 9, 10, 11, 13, 15 and 20 μM, respectively. The instrument is fluorospectrophotometer, model: LS 55.

EXAMPLE 5 pH Effect on the Detection of Fluorescence Probe Compound RPd1 for $Pd^{2-}$

Figure 4:
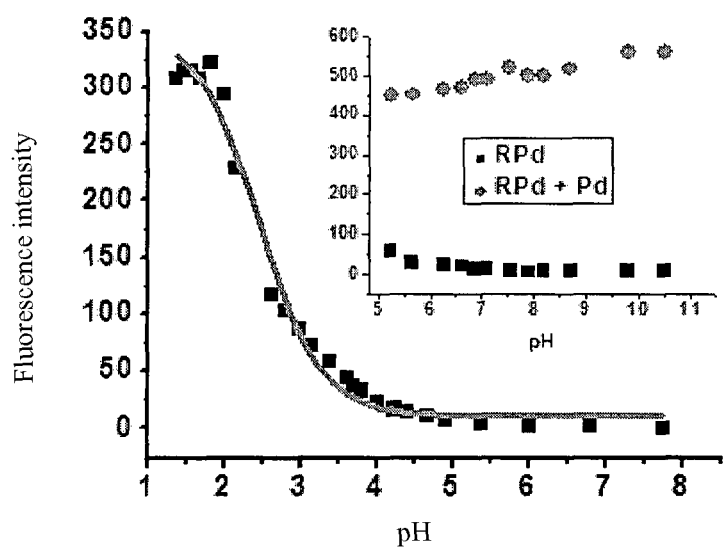
FIG. 4 is fluorescence emission spectra of RPd1 and RPd1-$Pd^{2+}$ coordination compound versus pH. X-axis is pH and Y-axis is fluorescence intensity. Concentration of RPd1 is 10 μM. pH is adjusted with NaOH (1M) and HCl (1M). The instrument is fluorospectrophotometer, model: LS 55.

The synthesized compound RPd1 was adopted to test the responses to different pH. The pH of RPd1 aqueous solution (ionic strength of 0.1) was adjusted to about 5.2, after measurement of fluorescence signal, a base solution was added to slowly adjust pH to 10.5 and the corresponding fluorescence signal change was measured, the result is shown in FIG. 4. From FIG. 4, it can be seen that, the fluorescence emission of the fluorescence probe compound RPd1 is nearly not affected by pH change in the range of 5.2 to 10.5. Therefore, the fluorescence probe compound RPd1 can be used for $Pd^{2+}$ detection within this pH range. X-axis is pH and Y-axis is fluorescence intensity. The concentrations of RPd1 and $Pd^{2+}$ were 10 μM, respectively. pH was adjusted by NaOH (1M) and HCl (1M). The instrument is fluorospectrophotometer, model: LS 55.

EXAMPLE 6

The Sensitivity of Fluorescence Probe Compound RPd1 to $Pd^{2+}$

Figure 5:
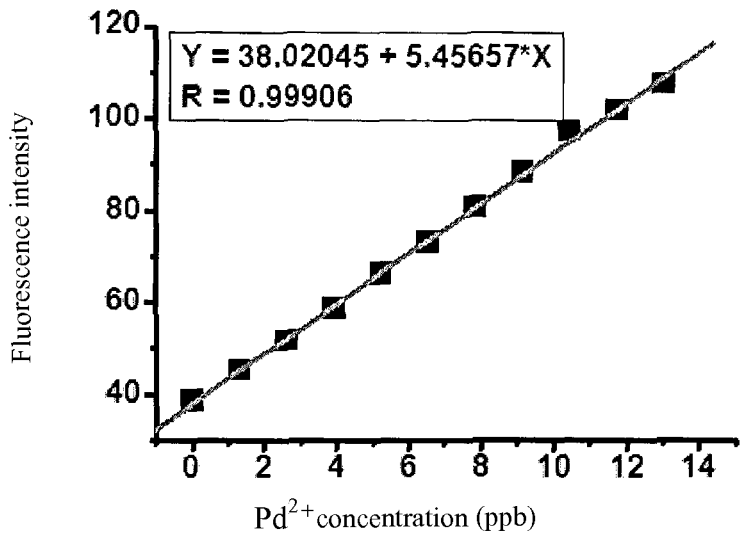
FIG. 5 shows linear relationship of fluorescence intensity of RPd1 versus $Pd^{2+}$ concentration in ppb level. Concentration of RPd1 is 10 μM. X-axis is $Pd^{2+}$ concentration and Y-axis is fluorescence intensity. The instrument is fluorospectrophotometer, model: LS 55.

The synthesized compound RPd1 was adopted to test the responses to $Pd^{2+}$ in ppb level. RPd1 (10 μM) was added into ethanol solution containing 0-10 ppb $Pd^{2+}$ followed by the measurement of corresponding fluorescence change, the result is shown in FIG. 5. From FIG. 5, it can be seen that, RPd1 displays an evident fluorescence enhancement when $Pd^{2+}$ is in the range of 0 to 10 ppb, and shows good linear relationship between fluorescence intensity and $Pd^{2+}$ concentration. Thus the fluorescence probe compound RPd1 can be used for $Pd^{2+}$ detection in low concentration. The instrument is fluorospectrophotometer, model: LS 55.

EXAMPLE 7

The Responses of RPd1 to Different Pd Species

Figure 6:
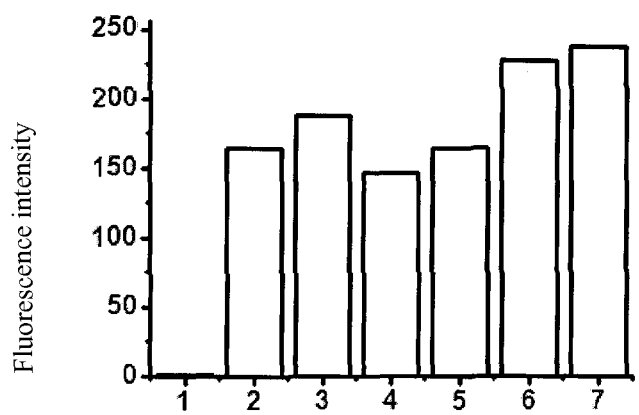
FIG. 6 shows recognition responses of RPd1 to different palladium salts. X-axis is palladium salt and Y-axis is fluorescence intensity. Concentrations of RPd1 and the palladium salts are 10 μM, respectively. The instrument is fluorospectrophotometer, model: LS 55.

FIG. 6 displays the different responses of RPd1 to different Pd species. X-axis is the different Pd species and Y-axis is fluorescence intensity. The concentrations of RPd1 and Pd species were 10 μM, respectively. The instrument is fluorospectrophotometer, model: LS 55.

EXAMPLE 8

The Reversibility of $Pd^{2+}$ Binding to RPd1

Figure 7:
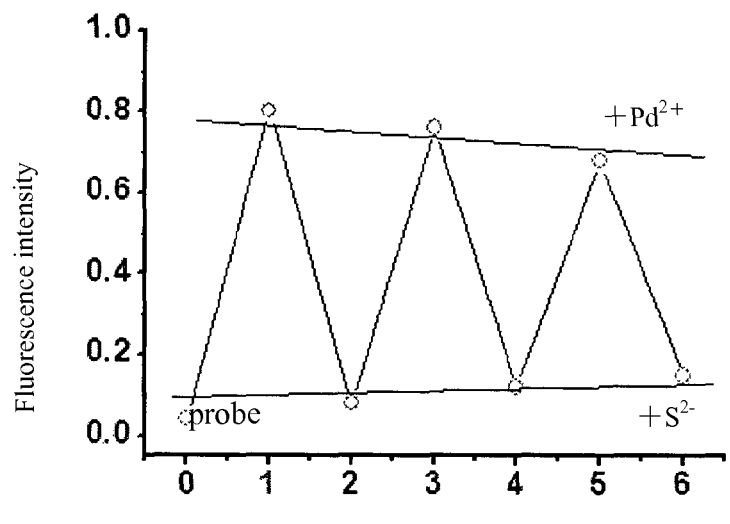
FIG. 7 shows reversibility of $Pd^{2+}$ binding to RPd1 checked by adding $Pd^{2+}$ and $S^{2-}$. Concentrations of RPd1 and $Pd^{2+}$ are 10 μM in $CH_2Cl_2$, respectively. Quenching process is done by washing the $CH_2Cl_2$ solution of RPd1-$Pd^{2+}$ by concentrated $Na_2S$ aqueous solution. X-axis is test sample and Y-axis is absorption intensity. The instrument is UV-visible spectrophotometer, model: HP8453.

FIG. 7 displays the reversibility of $Pd^{2+}$ binding to RPd1 checked by adding $Pd^{2+}$ and $S^{2-}$. The concentrations of RPd1 and $Pd^{2+}$ were both 10 μM in $CH_2Cl_2$. The quenching process was done by washing the $CH_2Cl_2$ solution of RPd1-$Pd^{2+}$ by $Na_2S$ aqueous solution. X-axis is test sample and Y-axis is absorption intensity. The instrument is UV-visible spectrophotometer, model: HP8453.

EXAMPLE 9

The Detection of Residual Palladium in Drug Sample by RPd1

Figure 8:
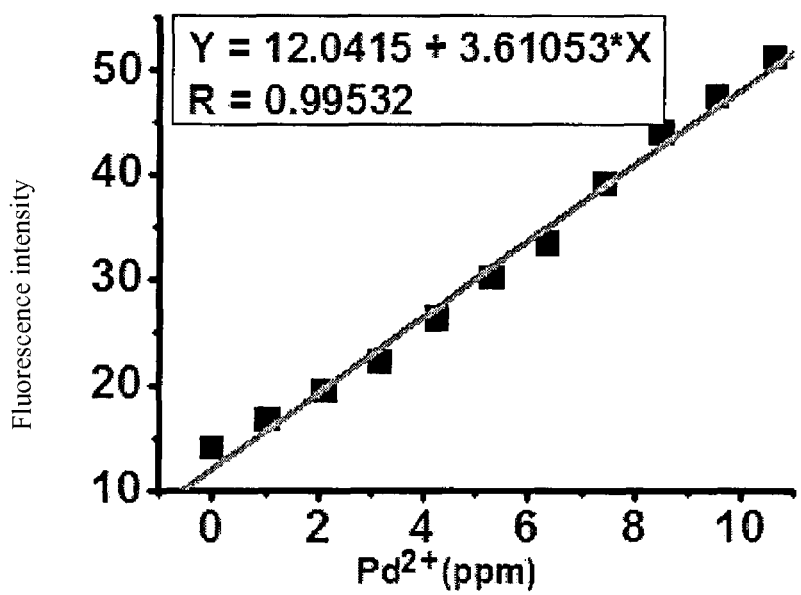
FIG. 8 shows detection of residual palladium in drug by RPd1. Paracetamol ethanol solution (10 mg/ml) from which insoluble ingredients were filtered is used. RPd1 (10 μM) is added into samples which contain $Pd^{2+}$ with different concentrations (0-10 ppm, calculated based on the weight of paracetamol), and then fluorescence signal is measured. X-axis is $Pd^{2+}$ concentration and Y-axis is fluorescence intensity. The instrument is fluorospectrophotometer, model: LS 55.

FIG. 8 displays the detection of residual palladium in drug sample by RPd1. Paracetamol ethanol solution (10 mg/ml) from which insoluble ingredients were filtered was used. RPd1 (10 μM) was added into samples which contain $Pd^{2+}$ with different concentrations (0-10 ppm, calculated based on the weight of paracetamol) and then the fluorescence signal was measured. X-axis is $Pd^{2+}$ concentration and Y-axis is fluorescence intensity. The instrument is fluorospectrophotometer, model: LS 55.

EXAMPLE 10

The Detection of Residual Palladium in Soil Sample by RPd1

Figure 9:
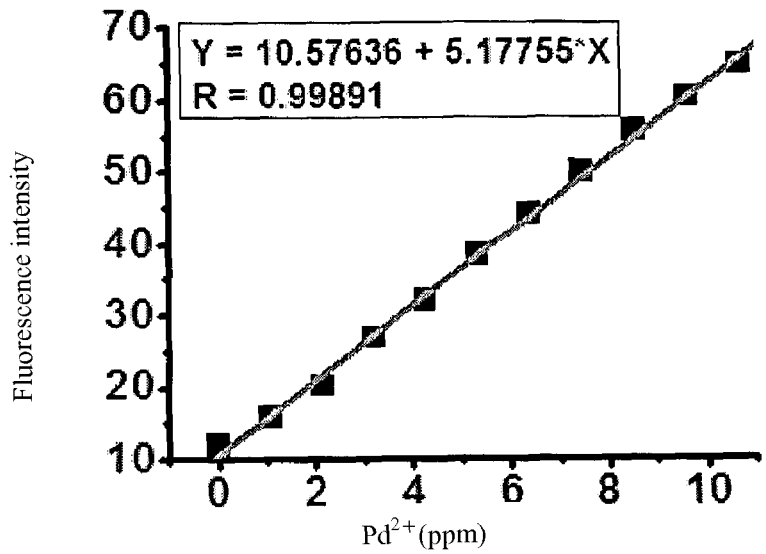
FIG. 9 shows detection of palladium in soil by RPd1. Soil ethanol solution (10 mg/ml) from which insoluble ingredients were filtered is used. RPd1 (10 μM) is added into samples which contain $Pd^{2+}$ with different concentrations (0-10 ppm, calculated based on the weight of soil), and then fluorescence signal is measured. X-axis is $Pd^{2+}$ concentration and Y-axis is fluorescence intensity. The instrument is fluorospectrophotometer, model: LS 55.

FIG. 9 displays the detection of residual palladium in soil sample by RPd1. Soil ethanol solution (10 mg/ml) from which insoluble ingredients were filtered was used RPd1 (10 μM) was added into samples which contain $Pd^{2+}$ with different concentrations (0-10 ppm, calculated based on the weight of soil), and then the fluorescence signal was measured. X-axis is $Pd^{2+}$ concentration and Y-axis is fluorescence intensity. The instrument is fluorospectrophotometer, model: LS 55.

EXAMPLE 11

The Residual Palladium Detection in Water Samples by RPd1

Figure 10:
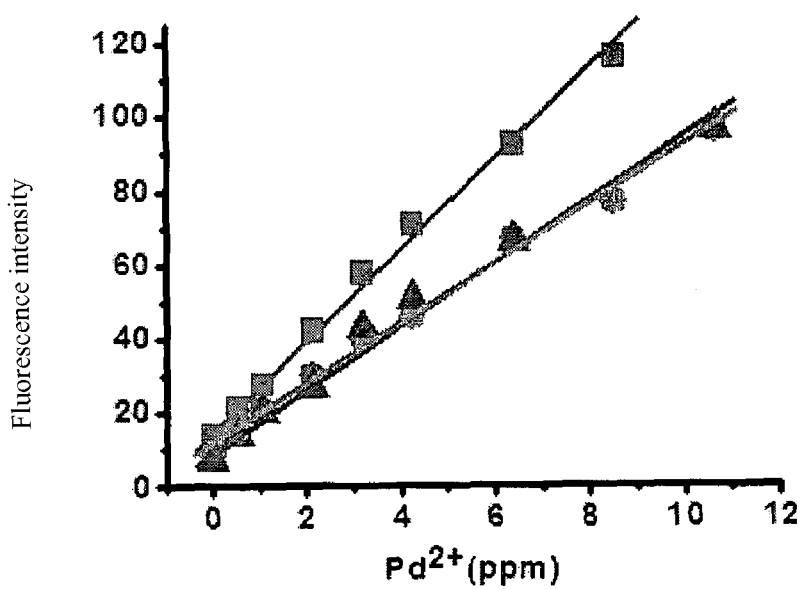
FIG. 10 shows detection of palladium in water sample by RPd1. Ethanolic water solution (50%) is used. RPd1 (10 μM) is added into samples which contain $Pd^{2+}$ with different concentrations (0-10 ppm, calculated based on the weight of water), and then fluorescence signal is measured. X-axis is $Pd^{2+}$ concentration and Y-axis is fluorescence intensity. The instrument is fluorospectrophotometer, model: LS 55.

FIG. 10 displays the detection of residual palladium in water sample by RPd1. Ethanolic water solution (50%) was used. RPd1 (10 μM) was added into samples which contain $Pd^{2+}$ with different concentrations (0-1 ppm, calculated based on the weight of water), and then the fluorescence signal was measured. X-axis is $Pd^{2+}$ concentration and Y-axis is fluorescence intensity. The instrument is fluorospectrophotometer, model: LS 55.

EXAMPLE 12

The Visual Detection of Residual Palladium in Reactor by RPd1

Figure 11:
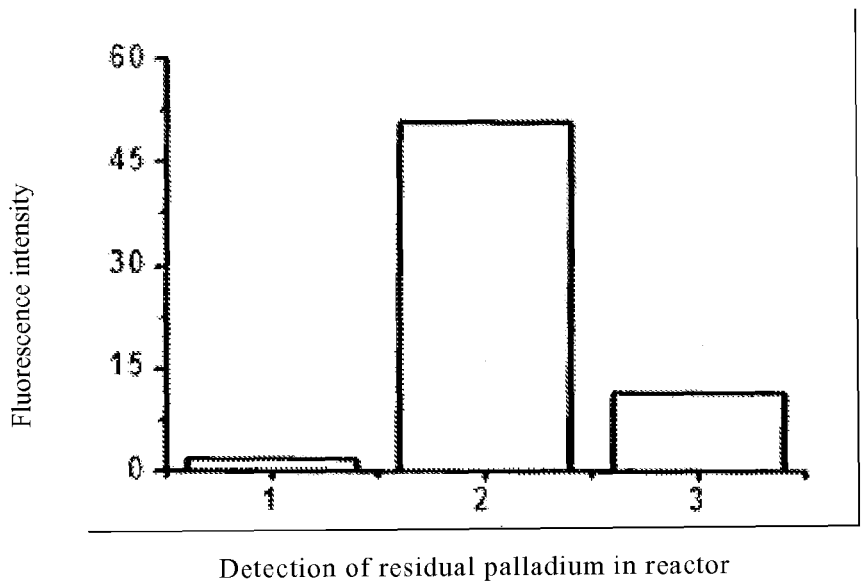
FIG. 11 shows visual detection of residual palladium in reactor by RPd1. X-axis is reactor number and Y-axis is fluorescence intensity. The instrument is fluorospectrophotometer, model: LS 55.
Figure 12:
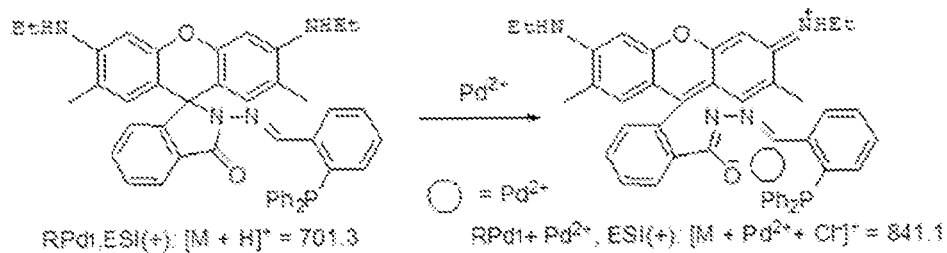
FIG. 12 shows $Pd^{2+}$ recognition mechanism of the probe in this invention.
Figure 13:
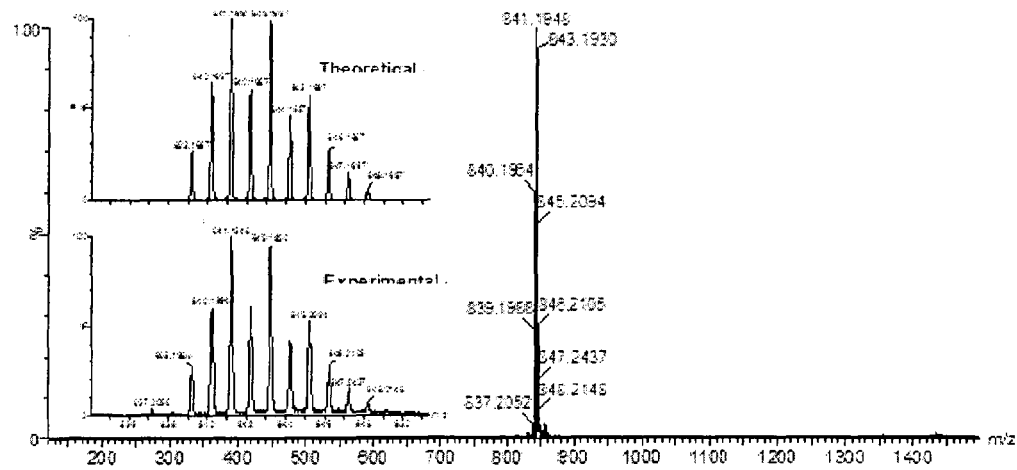
FIG. 13 is high-resolution mass spectrum identifying the 'ring-open' reaction of the probe in this invention induced by $Pd^{2+}$ coordination. TOF MS (ES): m/z Calcd for $C_{45}H_{41}ClN_4O_2PPd^+$: 841.1 (molecular weight of probe+$Pd^{2+}+Cl^-$). Found: 841.2.

$K_2CO_3$ (10 mg) and THF (10 ml) were added to three reactors. $PdCl_2$ and $Pd(AcO)_2$ (10 mg in both cases) were then added into two of the three reactors, respectively. The mixtures were stirred at room temperature for 1 h and then removed from the reactor. The reactors were brushed with detergent solution, then washed with water and acetone for three times, respectively. RPd1 ethanol solution (10 μM) was added into these reactors and stirred, and then the fluorescence measurement was performed, the result is shown in FIG. 11.

EXAMPLE 13

The Synthesis of Fluorescence Probe Compound RPd2

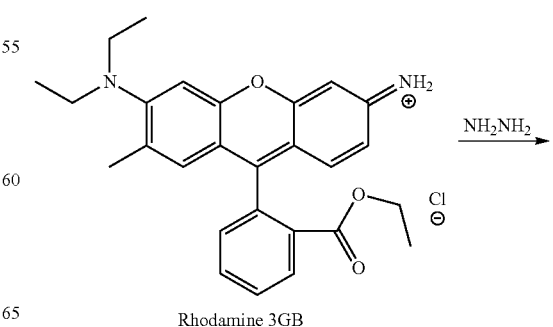

Rhodamine 3GB

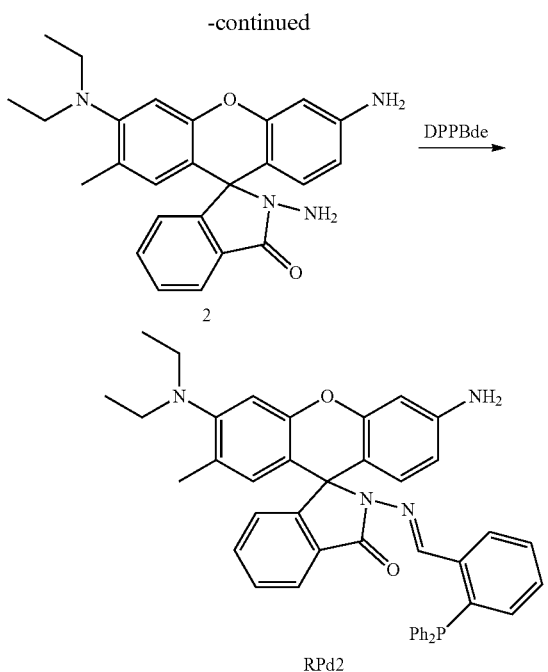

2.09 (s, 3H, CH$_3$), 1.26 (t, 6H, J=6.4 Hz, CH$_3$); $^{13}$C NMR (100 MHz, CDCl$_3$), δ$_C$ (ppm): 164.66, 152.88, 150.96, 147.46, 145.06, 140.01, 137.40, 134.91, 133.65, 130.14, 128.98, 128.30, 127.88, 126.31, 125.15, 122.88, 118.06, 106.17, 96.40, 66.88, 61.20, 38.44, 33.42, 29.81, 25.82, 23.45, 20.66, 17.31, 15.20, 13.72. TOF MS (ES): m/z Calcd for C$_{44}$H$_{40}$N$_4$O$_2$P$^+$: 687.2885. Found: 687.2877.

EXAMPLE 14

Selectivity Test of Fluorescence Probe Compound RPd2 to Pd$^{2+}$

Figure 14:
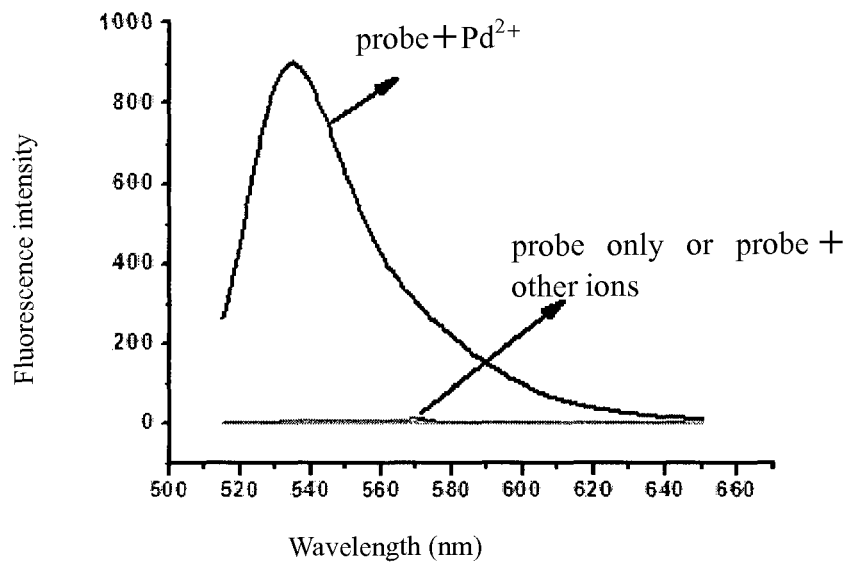
FIG. 14 is fluorescence emission spectrum of fluorescence probe compound RPd2 coordinating $Pd^{2+}$ over other common metal ion. Concentrations of RPd2 and the metal ions are 10 μM, respectively. X-axis is wavelength (nm) and Y-axis is fluorescence intensity. The instrument is fluorospectrophotometer, model: LS 55.

The synthesized compound RPd2 was adopted to test the selectivity to Pd$^{2+}$. RPd2 (10 μM) was added into ethanol solution containing the same amount of metal ion, the result is shown in FIG. 14. From FIG. 14, it can be seen that, RPd2 exhibits good selectivity to Pd$^{2+}$ and large fluorescence and UV absorption enhancement is induced by Pd$^{2+}$ without the interference from Na$^+$, K$^+$, Ca$^{2+}$, Mg$^{2+}$, Cu$^{2+}$ and so on. The instrument is fluorospectrophotometer, model: LS 55.

EXAMPLE 15

The Synthesis of Fluorescence Probe Compound RPd3

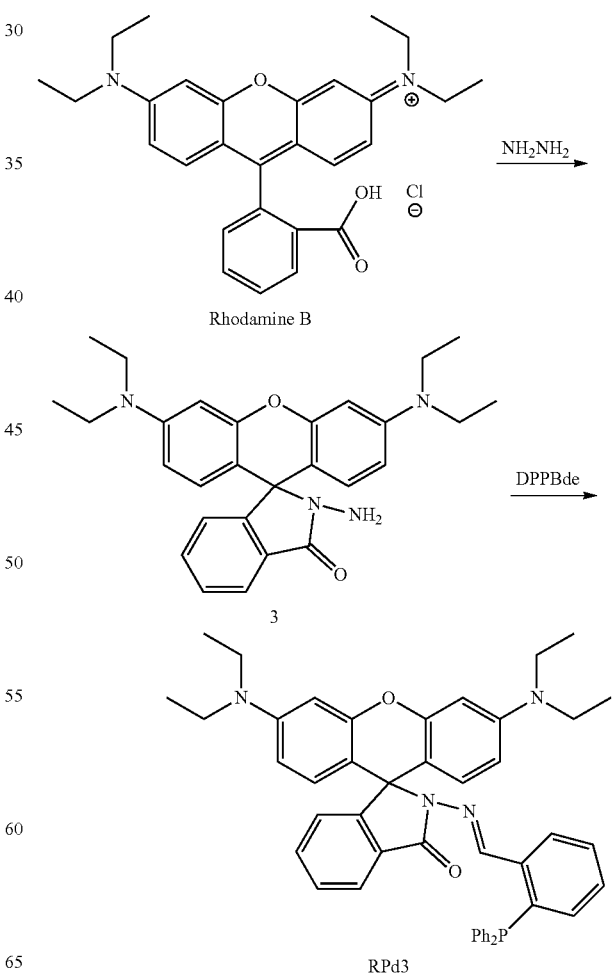

(1) The Synthesis of Intermediate 2

Rhodamine 3GB (1.16 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.67 g intermediate 2, yield 65.0%. $^1$H NMR (400 MHz CDCl$_3$) δ (ppm): 1.25 (t, 6H), 1.97 (s, 3H), 3.14 (t, 4H), 4.23 (s, 2H), 5.81 (s, 2H), 6.01 (s, 2H), 6.10 (m, 1H), 6.27 (s, 2H), 6.95 (d, J=8 Hz, 1H), 7.47 (d, J=8 Hz, 1H), 7.48 (d, J=8 Hz, 1H), 7.85 (t, 1H); $^{13}$C NMR (400 MHz, CDCl$_3$), δ: 12.7, 19.8, 44.5, 66.04, 98.09, 103.78, 108.17, 109.9, 123.98, 124.07, 126.58, 128.62, 134.97, 149.21, 152.64, 152.87, 165.87; TOF MS (ES): m/z Calcd for C$_{25}$H$_{26}$N$_4$O$_2^+$: 414.2056. Found: 414.2072.

(2) The Synthesis of Fluorescence Probe Compound RPd2:

The intermediate 2 (0.20 g, 0.5 mmol) and 2-diphenylphosphinobenzaldehyde (DPPBde, 0.15 g, 0.5 mmol) were added into a 100 ml single-necked flask and then 50 ml ethanol was added. The mixture was refluxed under stirring for 10 h in nitrogen environment, and then the solvent was removed under reduced pressure. The product was purified through column chromatography with CH$_2$Cl$_2$/EtOAc (v/v, 5/1) as elution solution to produce 0.24 g light pink solid RPd2, yield 69.3%. $^1$H NMR (400 MHz, CDCl$_3$), δ (ppm): 9.22 (d, 1H, J=6.4 Hz, NNCH), 8.18 (s, 1H, C$_6$H$_4$), 7.89 (d, 1H, C$_6$H$_4$), 7.41 (s, 2H, C$_6$H$_4$), 7.31 (d, 3H, J=7.2 Hz, C$_6$H$_4$), 7.22 (d, 4H, J=7.6 Hz, C$_6$H$_4$), 7.09 (t, 1H, J=7.2 Hz, C$_6$H$_4$), 6.99 (t, 5H, J=6.4 Hz, C$_6$H$_4$), 6.82 (s, 1H, C$_6$H$_4$), 6.33 (s, 2H, Xanthene-H), 6.28 (s, 2H, Xanthene-H), 3.12 (q, 4H, J=6.8 Hz, CH$_2$), (1) The Synthesis of Intermediate 3:

Rhodamine B (1.2 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.63 g intermediate 3, yield 55.3%. $^1$H NMR (400 MHz CDCl$_3$) δ (ppm): 1.15 (t, 12H), 3.31 (q, 8H), 3.60 (s, 2H), 6.25 (d, J=8 Hz, 2H), 6.45 (m, 4H), 7.07 (d, J=8 Hz, 1H), 7.45 (m, 1H), 7.47 (d, J=16 Hz, 1H), 8.02 (d, J=8 Hz, 1H), 9.42 (d, J=8 Hz, 1H); $^{13}$C NMR (400 MHz, CDCl$_3$), δ: 12.6, 44.5, 66.0, 98.0, 103.8, 108.1, 123.9, 124.0, 127.50, 128.62, 134.97, 147.22, 149.1, 152.6, 165.8; TOF MS (ES): m/z Calcd for $C_{28}H_{32}N_4O_2^+$: 456.2525. Found: 456.2536.

(2) The Synthesis of Fluorescence Probe Compound RPd3:

The intermediate 3 (0.23 g, 0.5 mmol) and 2-diphenylphosphinobenzaldehyde (DPPBde, 0.15 g, 0.5 mmol) were added into a 100 ml single-necked flask, and then 50 ml ethanol was added. The mixture was refluxed under stirring for 10 h in nitrogen environment, and then the solvent was removed under reduced pressure. The product was purified through column chromatography with CH$_2$Cl$_2$/EtOAc (v/v, 5/1) as elution solution to produce 0.27 g light pink solid RPd3, yield 75.3%. $^1$H NMR (400 MHz, CDCl$_3$), δ (ppm): 9.30 (d, 1H, J=6.4 Hz, NNCH), 8.24 (s, 1H, C$_6$H$_4$), 7.79 (d, 1H, C$_6$H$_4$), 7.39 (s, 2H, C$_6$H$_4$), 7.28 (d, 3H, J=7.2 Hz, C$_6$H$_4$), 7.18 (d, 4H, J=7.6 Hz, C$_6$H$_4$), 7.07 (t, 1H, J=7.2 Hz C$_6$H$_4$), 7.01 (t, 5H, J=6.4 Hz, C$_6$H$_4$), 6.79 (s, 1H, C$_6$H$_4$), 6.32 (s, 2H, Xanthene-H), 6.26 (s, 2H, Xanthene-H), 3.02 (q, 8H, J=6.8 Hz, CH$_2$), 1.20 (t, 12H, J=6.4 Hz, CH$_3$); $^{13}$C NMR (100 MHz, CDCl$_3$), δ$_C$ (ppm): 163.89, 153.28, 151.06, 148.26, 145.05, 139.81, 137.30, 135.45, 132.64, 130.24, 128.88, 128.10, 127.28, 126.31, 125.55, 123.42, 117.66, 107.23, 98.62, 67.58, 39.43, 34.51, 28.39, 25.78, 22.88, 21.06, 16.31, 14.50, 12.92. TOF MS (ES): m/z Calcd for $C_{47}H_{46}N_4O_2P^+$: 729.3385. Found: 729.3372.

EXAMPLE 16

Selectivity Test of Fluorescence Probe Compound RPd3 to Pd$^{2+}$

Figure 15:
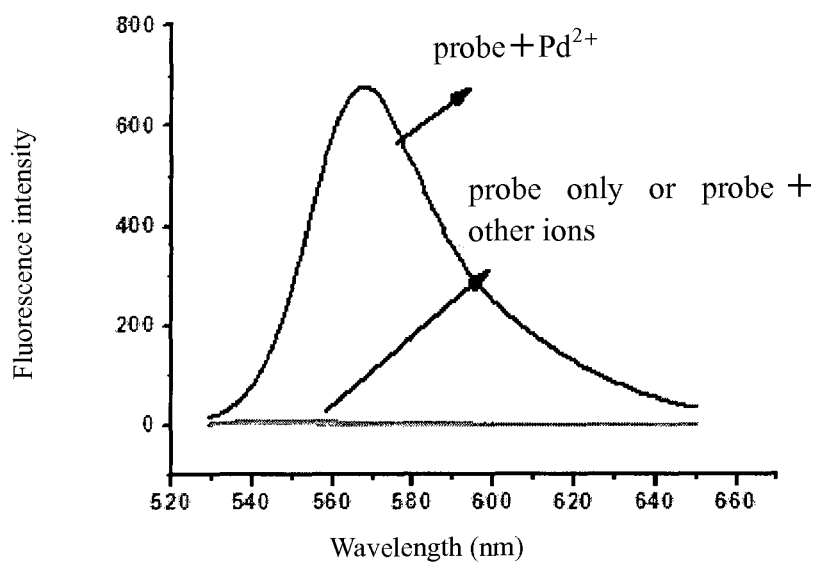
FIG. 15 is fluorescence emission spectrum of fluorescence probe compound RPd3 coordinating $Pd^{2+}$ over other common metal ion. Concentrations of RPd3 and the metal ions are 10 μM, respectively. X-axis is wavelength (nm) and Y-axis is fluorescence intensity. The instrument is fluorospectrophotometer, model: LS 55.

The synthesized compound RPd3 was adopted to test the selectivity to Pd$^{2+}$. RPd3 (10 μM) was added into ethanol solution containing the same amount of metal ion, the result is shown in FIG. 15. From FIG. 15, it can be seen that, RPd3 exhibits good selectivity to Pd$^{2+}$, and large fluorescence and UV absorption enhancement is induced by Pd$^{2+}$ without the interference from Na$^+$, K$^+$, Ca$^{2+}$, Mg$^{2+}$, Cu$^{2+}$ and so on. The instrument is fluorospectrophotometer, model: LS 55.

EXAMPLE 17

The Synthesis of Fluorescence Probe Compound RPd4

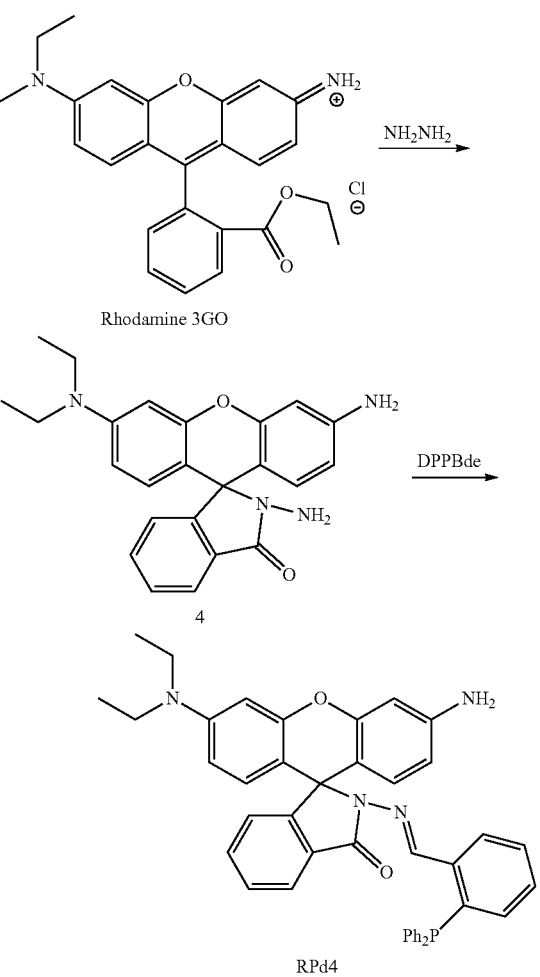

(1) The Synthesis of Intermediate 4:

Rhodamine 3GO (1.1 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.65 g intermediate 4, yield 65.0%. $^1$H NMR (400 MHz CDCl$_3$) δ (ppm): 1.18 (t, 6H), 3.35 (q, 4H), 3.62 (s, 2H), 5.85 (s, 2H), 6.14 (d, J=8 Hz, 2H), 6.25 (m, 4H), 7.10 (d, J=8 Hz, 1H), 7.48 (t, 2H), 8.02 (d, J=8 Hz, 1H); $^{13}$C NMR (400 MHz, CDCl$_3$), δ: 12.7, 18.89, 44.5, 66.04, 98.09, 103.78, 108.17, 123.98, 124.07, 126.58, 128.62, 134.97, 149.21, 152.64, 152.87, 165.87; TOF MS (ES): m/z Calcd for $C_{24}H_{24}N_4O_2^+$: 400.1899. Found: 400.1886.

(2) The Synthesis of Fluorescence Probe Compound RPd4:

The intermediate 4 (0.20 g, 0.5 mmol) and 2-diphenylphosphinobenzaldehyde (DPPBde, 0.15 g, 0.5 mmol) were added into a 100 ml single-necked flask, and then 50 ml ethanol was added. The mixture was refluxed under stirring for 10 h in nitrogen environment, and then the solvent was removed under reduced pressure. The product was purified through column chromatography with $CH_2Cl_2$/EtOAc (v/v, 5/1) as elution solution to produce 0.24 g light pink solid RPd4, yield 70.5%. $^1$H NMR (400 MHz, CDCl$_3$), δ (ppm): 9.22 (d, 1H, J=6.4 Hz, NNCH), 8.14 (s, 1H, $C_6H_4$), 7.80 (d, 1H, $C_6H_4$), 7.41 (s, 2H, $C_6H_4$), 7.29 (d, 3H, J=7.2 Hz, $C_6H_4$), 7.20 (d, 4H, J=7.6 Hz, $C_6H_4$), 7.09 (t, 1H, J=7.2 Hz $C_6H_4$), 7.03 (t, 5H, J=6.4 Hz, $C_6H_4$), 6.81 (s, 1H, $C_6H_4$), 6.35 (s, 2H, Xanthene-H), 6.24 (s, 2H, Xanthene-H), 3.12 (q, 4H, J=6.8 Hz, $CH_2$), 1.29 (t, 6H, J=6.4 Hz, $CH_3$); $^{13}$C NMR (100 MHz, CDCl$_3$), $δ_C$ (ppm): 164.19, 153.33, 151.12, 148.55, 144.95, 139.88, 137.38, 134.85, 132.54, 130.62, 129.38, 128.18, 127.02, 126.42, 125.66, 122.72, 117.76, 108.84, 97.63, 67.68, 38.52, 33.42, 28.40, 25.82, 23.38, 20.76, 16.86, 15.53, 12.80. TOF MS (ES): m/z Calcd for $C_{43}H_{38}N_4O_2P^+$: 673.2729. Found: 627.2738.

EXAMPLE 18

Selectivity Test of Fluorescence Probe Compound RPd4 to $Pd^{2+}$

Figure 16:
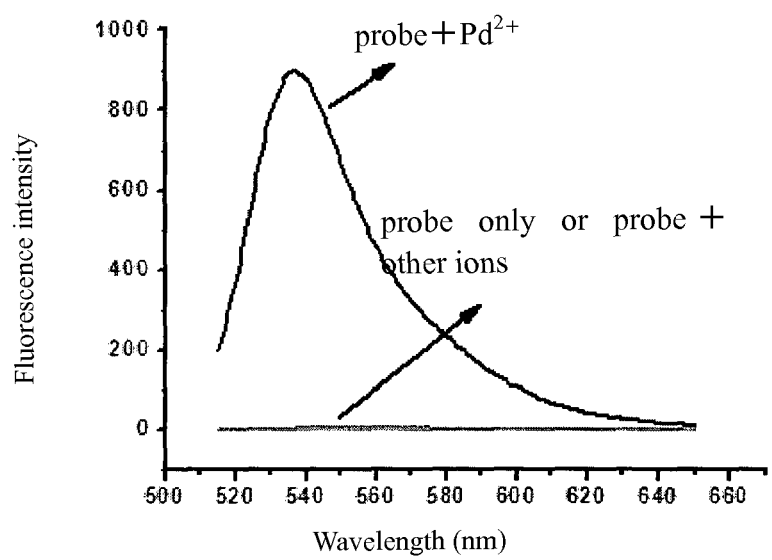
FIG. 16 is fluorescence emission spectrum of fluorescence probe compound RPd4 coordinating $Pd^{2+}$ over other common metal ion. Concentrations of RPd4 and the metal ions are 10 μM, respectively. X-axis is wavelength (nm) and Y-axis is fluorescence intensity. The instrument is fluorospectrophotometer, model: LS 55.
Figure 17:
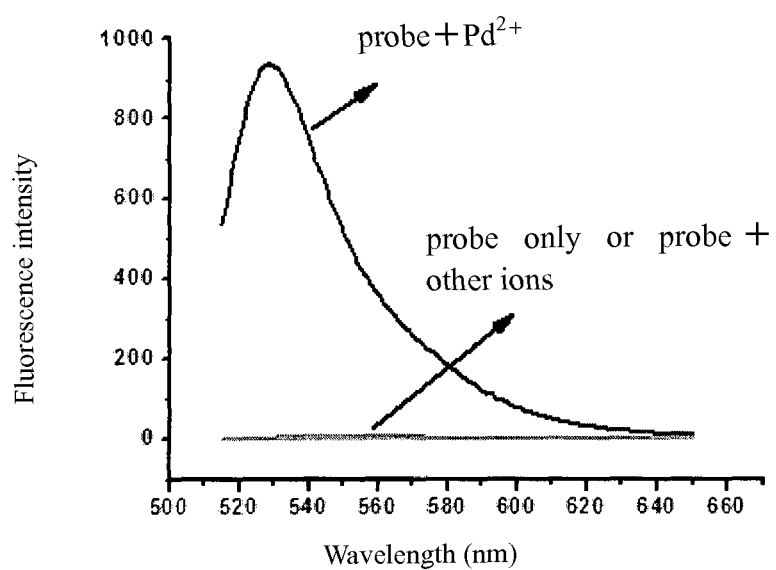
FIG. 17 is fluorescence emission spectrum of fluorescence probe compound RPd5 coordinating $Pd^{2+}$ over other common metal ion. Concentrations of RPd5 and the metal ions are 10 μM, respectively. X-axis is wavelength (nm) and Y-axis is fluorescence intensity. The instrument is fluorospectrophotometer, model: LS 55.

The synthesized compound RPd4 was adopted to test the selectivity to $Pd^{2+}$. RPd4 (10 μM) was added into ethanol solution containing the same amount of metal ion, the result is shown in FIG. 16. From FIG. 16, it can be seen that, RPd4 exhibits good selectivity to $Pd^{2+}$, and large fluorescence and UV absorption enhancement is induced by $Pd^{2+}$ without the interference from $Na^+$, $K^+$, $Ca^{2+}$, $Mg^+$, $Cu^{2+}$ and so on. The instrument is fluorospectrophotometer, model: LS 55.

EXAMPLE 19

The Synthesis of Fluorescence Probe Compound RPd5

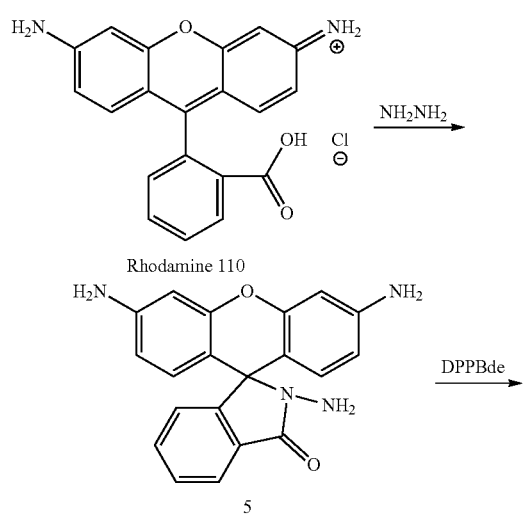

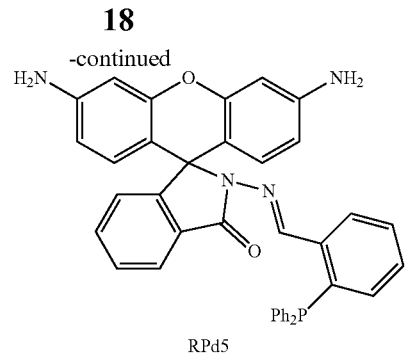

RPd5

(1) The Synthesis of Intermediate 5:

Rhodamine 110 (0.9 g, 2.5 mmol) was added into a 100 ml single-necked flask containing 30 ml ethanol. The mixture was stirred vigorously at room temperature, followed by dropwise addition of excessive amount of 85% hydrazine hydrate solution (3 ml). After finishing the addition of hydrazine hydrage, the mixture was refluxed for 2 h in air until the solution changed from purple to light brown in color and finally became clear. Then the solution was cooled down to room temperature and ethanol was removed under reduced pressure. After that, 50 ml HCl (1 M) was added to give a red solution, and then 70 ml NaOH aqueous solution (1 M) was added under stirring to adjust pH to 9 to 10 to form a large amount of precipitation. The precipitation was filtered and washed with 15 ml water for three times, then dried under vacuum and purified through column chromatography to produce 0.52 g intermediate 5, yield 60.0%. $^1$H NMR (400 MHz CDCl$_3$) δ (ppm): 3.62 (s, 2H), 5.85 (s, 4H), 6.14 (d, J=8 Hz, 2H), 6.25 (m, 4H), 7.10 (d, J=8 Hz, 1H), 7.48 (t, 2H), 8.02 (d, J=8 Hz, 1H); $^{13}$C NMR (400 MHz, CDCl$_3$), δ (ppm): 66.04, 98.09, 103.78, 108.17, 123.98, 124.07, 126.58, 128.62, 134.97, 149.21, 152.64, 152.87, 165.87; TOF MS (ES): m/z Calcd for $C_{20}H_{17}N_4O_2^+$: 345.1346. Found: 345.1351.

(2) The Synthesis of Fluorescence Probe Compound RPd5:

The intermediate 5 (0.17 g, 0.5 mmol) and 2-diphenylphosphinobenzaldehyde (DPPBde, 0.15 g, 0.5 mmol) were added into a 100 ml single-necked flask and then 50 ml ethanol was added. The mixture was refluxed under stirring for 10 h in nitrogen environment, and then the solvent was removed under reduced pressure. The product was purified through column chromatography with $CH_2Cl_2$/EtOAc (v/v, 5/1) as elution solution to produce 0.24 g light pink solid RPd5, yield 76.5% $^1$H NMR (400 MHz, CDCl$_3$), δ (ppm): 9.19 (d, 1H, J=6.4 Hz, NNCH), 8.22 (s, 1H, $C_6H_4$), 7.86 (d, 1H, $C_6H_4$), 7.42 (s, 2H, $C_6H_4$), 7.27 (d, 3H, J=7.2 Hz, $C_6H_4$), 7.18 (d, 4H, J=7.6 Hz, $C_6H_4$), 7.08 (t, 1H, J=7.2 Hz $C_6H_4$), 7.02 (t, 5H, J=6.4 Hz, $C_6H_4$), 6.71 (s, 1H, $C_6H_4$), 6.45 (s, 2H, Xanthene-H), 6.33 (s, 2H, Xanthene-H), 4.52 (s, 4H, $NH_2$); $^{13}$C NMR (100 MHz, CDCl$_3$), $δ_C$ (ppm): 164.19, 153.33, 151.12, 148.55, 144.95, 139.88, 137.38, 134.85, 132.54, 130.62, 129.38, 128.18, 127.02, 126.42, 125.66, 122.72, 117.76, 108.84, 97.63, 67.68, 38.52, 33.42, 28.40, 25.82, 23.38, 20.76. TOF MS (ES): m/z Calcd for $C_{39}H_{30}N_4O_2P^+$: 617.2112. Found: 617.2120.

EXAMPLE 20

Selectivity Test of Fluorescence Probe Compound RPd5 to $Pd^{2+}$

The synthesized compound RPd5 was adopted to test the selectivity to $Pd^{2+}$. RPd5 (10 μM) was added into ethanol solution containing the same amount of metal ion, the result is

The invention claimed is:

1. A fluorescence probe compound of general formula I:

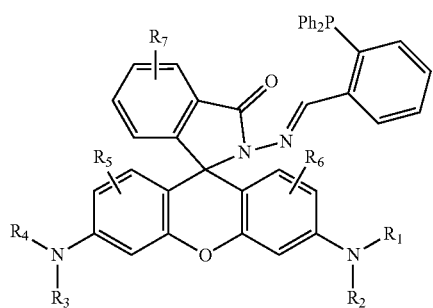

I wherein
$R_1$, $R_2$, $R_3$ and $R_4$ are each independently selected from the group consisting of H, $C_{1-6}$ alkyl, $C_{1-6}$ alkyl substituted phenyl, $C_{1-6}$ alkyl substituted naphthyl, halogen, $OR_8$, $N(R_8)_2$, CN, $(CH_2CH_2O)_nH$, $(CH_2)_mCOOM$ and $(CH_2)_mSO_3M$;

$R_5$, $R_6$ and $R_7$ are each independently selected from the group consisting of H, $C_{1-6}$ alkyl, $C_{1-6}$ alkyl substituted phenyl, $C_{1-6}$ alkyl substituted naphthyl, halogen, hydroxyl, mercapto group, cyano group, nitro group, heterocyclic group, halogenated alkyl, alkyl amino group, acylamino group, $OR_8$, $N(R_8)_2$, $(CH_2CH_2O)_nH$, $(CH_2)_mCOOM$ and $(CH_2)_mSO_3M$;

$R_8$ is selected from the group consisting of H, $C_{1-6}$ alkyl, $C_{1-6}$ alkyl substituted phenyl, $C_{1-6}$ alkyl substituted naphthyl, halogen, CN, $(CH_2CH_2O)_nH$, $(CH_2)_mCOOM$ and $(CH_2)_mSO_3M$;

n and m are integer from 0 to 6;

M is selected from the group consisting of H, K, Na, Li, $NH_4$, $NH_3R_9$, $NH_2(R_9)_2$, $NH(R_9)_3$ and $N(R_9)_4$;

and $R_9$ is selected from the group consisting of H, $C_{1-6}$ alkyl and $CH_2CH_2OH$.

2. A preparation method of the fluorescence probe compound according to claim 1, comprising the steps of:
(1) synthesizing an intermediate of formula II by reacting a rhodamine fluorescence dye of formula with lactone-ring and hydrazine hydrate; and

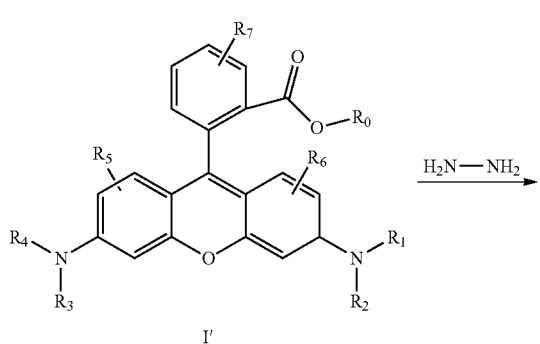

I'

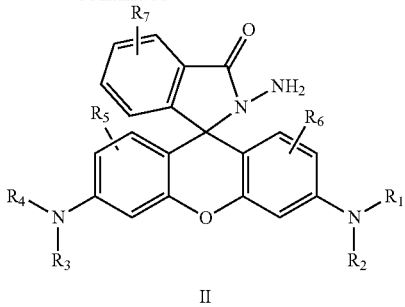

II (2) synthesizing the compound of general formula I by reacting the intermediate II obtained in (1) and 2-diphenylphosphinobenzaldehyde

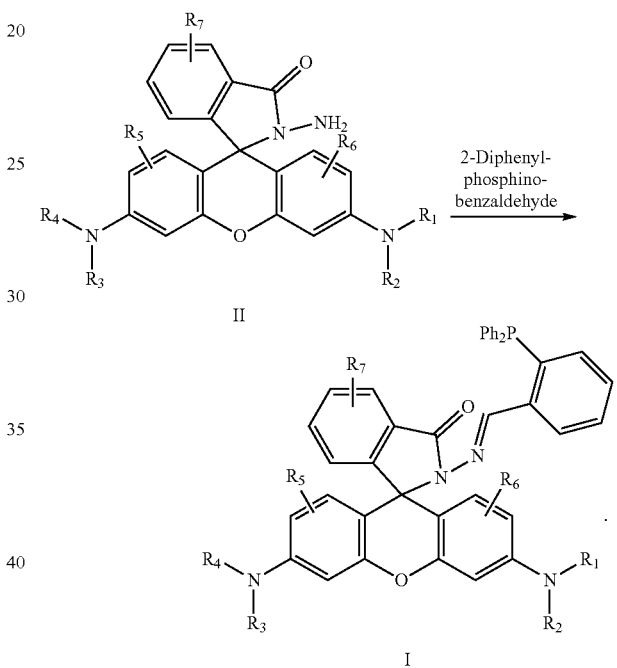

3. The preparation method according to claim 2, wherein the rhodamine fluorescence dye is selected from the group consisting of rhodamine B, rhodamine 110, rhodamine 6G, rhodamine 3GB, rhodamine 3GO, and rhodamine 123.

4. The preparation method of claim 2, wherein step (1) further comprises the substeps of:
adding the rhodamine fluorescence dye of formula and an stoichiometrically excessive amount of hydrazine hydrate into an alcohol solvent at room temperature to obtain a solution;
refluxing the solution to obtain a clear reaction solution;
cooling the clear solution to room temperature;
removing the solvent from the clear solution by evaporation;
adding an acid to the resulting solution to a pH value of 2 to 5;
adjusting the pH value to 9 to 10 by to form a precipitate; and
filtering, washing, drying, and optionally recrystallizing the precipitate to obtain the intermediate II.

5. The preparation method of claim 2, wherein step (2) further comprises the substeps of:

mixing the intermediate II obtained in step (1) and a stoichiometric amount of 2-diphenylphosphinobenzaldehyde in ethanol to obtain a mixture;

refluxing the mixture for 5 to 10 h;

removing the solvent from the mixture by evaporation; and separating a resulting mixture by column chromatography to obtain the fluorescence probe compound of general formula I.

6. A method of detecting palladium in a sample, comprising the step of:

adding a fluorescence probe compound of general formula I according to claim 1 into the sample to obtain a sample mixture; and measuring a fluorescence signal from the sample mixture.

7. The method of claim 6, wherein the sample is a drug sample, a soil sample, a water sample, or a material from a reaction vessel.

8. The method of claim 6, wherein a concentration of palladium in the sample mixture is less than 10 ppb or less than 5 nM.

* * * * *